United States Patent [19]

Chang et al.

[11] Patent Number: 5,449,847
[45] Date of Patent: Sep. 12, 1995

[54] SELECTIVE CONVERSION OF BENZENE TO TERCYCLOHEXANE

[75] Inventors: Clarence D. Chang, Princeton; Scott Han, Lawrenceville; John D. Lutner, Hamilton Square, all of N.J.; Jose G. Santiesteban, Yardley, Pa.

[73] Assignee: Mobil Oil Corporation, Fairfax, Va.

[21] Appl. No.: 228,772

[22] Filed: Apr. 18, 1994

[51] Int. Cl.⁶ .......................... C07C 5/10; C07C 13/00
[52] U.S. Cl. ..................................... 585/266; 585/268; 585/350; 585/360; 585/375
[58] Field of Search ............... 585/350, 360, 375, 266, 585/268

[56] References Cited

U.S. PATENT DOCUMENTS

| | | | |
|---|---|---|---|
| 4,175,033 | 11/1979 | Hilfman | 208/143 |
| 4,534,883 | 8/1985 | Sugimori et al. | 252/299.63 |
| 4,663,073 | 5/1987 | Sucrow et al. | 252/299.63 |
| 4,839,267 | 6/1989 | Monbaliu et al. | 430/546 |
| 4,840,745 | 6/1989 | Tsubouchi et al. | 252/73 |
| 4,911,823 | 3/1990 | Chen et al. | 208/67 |
| 4,926,000 | 5/1990 | Morrison | 585/476 |
| 4,990,239 | 2/1991 | Derr, Jr. et al. | 208/68 |
| 5,113,034 | 5/1992 | Soled et al. | 585/510 |

FOREIGN PATENT DOCUMENTS 1-288339  7/1989  Japan.
0825473  5/1981  U.S.S.R.
94/14732  7/1994  WIPO.

OTHER PUBLICATIONS

Hino, M. et al., "Synthesis of Solid Superacid of Tungsten Oxide supported on Zirconia and its Catalytic Action for Reactions of Butane and Pentane," J. Chem. Soc. Chem. Comm., 1259–1260 (1988).

Arata, K. et al., "Synthesis of Solid Superacid of Tungsten Oxide Supported on Zirconia and Its Catalytic Action," Proceedings 9th International Congress on Catalysis, 4, 1727–1735 (1988).

Primary Examiner—P. Achutamurthy
Attorney, Agent, or Firm—Alexander J. McKillop; Dennis P. Santini; Lori F. Cuomo

[57] ABSTRACT

There is provided a process for preparing tercyclohexane by reacting benzene with hydrogen. The process involves the use of a catalyst comprising an acidic solid and a hydrogenation component. The acidic solid may comprise a Group IVB metal oxide, such as zirconia, modified with an oxyanion of a Group VIB metal, such as tungsten. The hydrogenation component may comprise platinum.

12 Claims, No Drawings

SELECTIVE CONVERSION OF BENZENE TO TERCYCLOHEXANE

BACKGROUND

There is provided a process for preparing tercyclohexane by reacting benzene with hydrogen. The process involves the use of a catalyst comprising an acidic solid and a hydrogenation component. The acidic solid may comprise a Group IVB metal oxide, such as zirconia, modified with an oxyanion of a Group VIB metal, such as tungsten. The hydrogenation component may comprise platinum.

Benzene has had a high value as a basic petrochemical. However, current and anticipated environmental regulations have provided an incentive to convert benzene to other chemicals.

A number of reactions are known for converting benzene to other chemicals using other reactants. Examples of such reactions include alkylation with olefins, alcohols or olefinic fragments from paraffin cracking, as well as transalkylations, e.g., with xylenes.

The Morrison U.S. Pat. No. 4,926,000 describes the conversion of benzene by reaction with itself over a ZSM-5 catalyst. The products of this benzene self-reaction include light gases, alkylbenzenes, naphthalenes, and alkylnaphthalenes. The addition of hydrogen to this reaction is said to result in greater light gas yield by ring hydrocracking. The reaction conditions disclosed in the Morrison patent are somewhat severe, including temperatures generally greater than 800° F. (427° C.).

The Hilfman U.S. Pat. No. 4,175,033; the Chen et al. U.S. Pat. No. 4,911,823; and the Derr, Jr., et al. U.S. Pat. No. 4,990,239 suggest that benzene in various hydrocarbon feed streams, when passed along with hydrogen under sufficient conditions over various zeolites containing hydrogenation components, may undergo hydrogenation and ring opening reactions.

As reported in the Abe et al. published European Patent Application No. 89/117750, tercyclohexane is useful as a traction-drive fluid. The Monbaliu et al. U.S. Pat. No. 4,839,267 discloses that tercyclohexane or butyltercyclohexane may be used as a water-immiscible, high-boiling, oil-type hydrocarbon solvent component of a photographic element. The Sugimori et al. U.S. Pat. No. 4,534,883 and the Sucrow et al. U.S. Pat. No. 4,663,073 describe the use of various functionalized derivatives of tercyclohexane as liquid crystals.

SUMMARY

There is provided a process for preparing tercyclohexane, said process comprising passing hydrogen and benzene under sufficient conversion conditions over a catalyst comprising an acidic solid and a hydrogenation component. There is also provided a process for preparing tercyclohexane, said process comprising the steps of:

(a) passing hydrogen and benzene under sufficient conversion conditions over a catalyst comprising an acidic solid and a noble metal, wherein said acidic solid comprises an oxide of zirconium modified with an oxyanion of tungsten; and
(b) recovering tercyclohexane.

EMBODIMENTS

Tercyclohexane may exist in the form of three possible positional isomers. These isomers are 1,1':4',1''-tercyclohexane; 1,1':3',1''-tercyclohexane; and 1,1':2',1''-tercyclohexane. The nomenclature for tercyclohexane is discussed in the *Kirk-Othmer Encyclopedia of Chemical Technology*, 3rd ed., 12, 897–898 (1980). In particular, the isomer, 1,1:4',1''-tercyclohexane [1795-19-3], is represented therein, along with the positions of the respective carbon atoms, as follows:

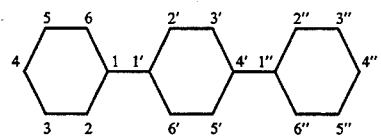

It will be understood that the present reaction is a hydrogenation reaction insofar as 7 moles of $H_2$ are needed to react with three moles of benzene ($C_6H_6$) in order to form 1 mole of tercyclohexane ($C_{18}H_{32}$).

The tercyclohexane product may be recovered from the effluent of the present reaction by any convenient means, such as by distillation. The tercyclohexane product so recovered may be at least substantially pure. For example, this product may contain at least 90 wt. % of tercyclohexane and less than 10 wt. % of impurities, such as hydrocarbons other than tercyclohexane.

The catalyst described herein may comprise an oxide of a Group IVB metal, preferably zirconia or titania. This Group IVB metal oxide may be modified in two ways. According to one modification, the Group IVB metal oxide may be modified with an oxyanion of a Group VIB metal, such as an oxyanion of tungsten, such as tungstate. The modification of the Group IVB metal oxide with the oxyanion of the Group VIB metal imparts acid functionality to the material. The modification of a Group IVB metal oxide, particularly, zirconia, with a Group VIB metal oxyanion, particularly tungstate, is described in U.S. Pat. No. 5,113,034; in Japanese Kokai Patent Application No. Hei 1 [1989]-288339; and in an article by K. Arata and M. Hino in *Proceedings* 9th International Congress on Catalysis, 4, 1727–1735 (1988), the entire disclosures of these publications are expressly incorporated herein by reference.

According to another modification of the Group IVB metal oxide described herein, a hydrogenation component is combined with the Group IV metal oxide. This hydrogenation component imparts the ability of the material to catalyze the addition of hydrogen to benzene.

Examples of hydrogenation components include the oxide, hydroxide or free metal (i.e., zero valent) forms of Group VIII metals (i.e., Pt, Pd, Ir, Rh, Os, Ru, Ni, Co and Fe); Group IVA metals (i.e., Sn and Pb); Group VB metals (i.e., Sb and Bi); and Group VIIB metals (i.e., Mn, Tc and Re). The present catalyst may comprise one or more catalytic forms of one or more noble metals (i.e., Pt, Pd, Ir, Rh, Os or Ru). Combinations of catalytic forms of such noble or non-noble metals, such as combinations of Pt with Sn, may be used. The valence state of the metal of the hydrogenation component is preferably in a reduced valance state, e.g., when this component is in the form of an oxide or hydroxide. The reduced valence state of this metal may be attained, in situ, during the course of a reaction, when a reducing agent, such as hydrogen, is included in the feed to the reaction.

For the purposes of the present disclosure, the expression, Group IVB metal oxide modified with an oxyanion of a Group VIB metal, is intended to connote a material comprising, by elemental analysis, a Group IVB metal, a Group VIB metal and oxygen, with more acidity than a simple mixture of separately formed Group IVB metal oxide mixed with a separately formed Group VIB metal oxide or oxyanion. The present Group IVB metal, e.g., zirconium, oxide modified with an oxyanion of a Group VIB metal, e.g., tungsten, is believed to result from an actual chemical interaction between a source of a Group IVB metal oxide and a source of a Group VIB metal oxide or oxyanion.

This chemical interaction is discussed in the aforementioned article by K. Arata and M. Hino in *Proceedings 9th International Congress on Catalysis*, 4, 1727–1735 (1988). In this article, it is suggested that solid superacids are formed when sulfates are reacted with hydroxides or oxides of certain metals, e.g., Zr. These superacids are said to have the structure of a bidentate sulfate ion coordinated to the metal, e.g., Zr. In this article, it is further suggested that a superacid can also be formed when tungstates are reacted with hydroxides or oxides of Zr. The resulting tungstate modified zirconia materials are theorized to have an analogous structure to the aforementioned superacids comprising sulfate and zirconium, wherein tungsten atoms replace sulfur atoms in the bidentate structure.

Although it is believed that tungstate-modified zirconia may comprise the bidentate structure suggested in the aforementioned article by Arata and Hino, the particular structure of the catalytically active site in the present Group IVB metal oxide modified with an oxyanion of a Group VIB metal has not yet been confirmed, and it is not intended that this catalyst component should be limited to any particular structure.

Other elements, such as alkali (Group IA) or alkaline earth (Group IIA) compounds may optionally be added to the present catalyst to alter catalytic properties. The addition of such alkali or alkaline earth compounds to the present catalyst may enhance the catalytic properties of components thereof, e.g., Pt or W, in terms of their ability to function as a hydrogenation component or an acid component.

The Group IVB metal (i.e., Ti, Zr or Hf) and the Group VIB metal (i.e., Cr, Mo or W) species of the present catalyst are not limited to any particular valence state for these species. These species may be present in this catalyst in any possible positive oxidation value for these species. Subjecting the catalyst, e.g., when the catalyst comprises tungsten, to reducing conditions, e.g., believed to be sufficient to reduce the valence state of the tungsten, may enhance the overall catalytic ability of the catalyst to catalyze certain reactions, e.g., the isomerization of n-hexane.

Suitable sources of the Group IVB metal oxide, used for preparing the present catalyst, include compounds capable of generating such oxides, such as oxychlorides, chlorides, nitrates, etc., particularly of zirconium or titanium. Alkoxides of such metals may also be used as precursors or sources of the Group IVB metal oxide. Examples of such alkoxides include zirconium n-propoxide and titanium i-propoxide. Preferred sources of a Group IVB metal oxide are zirconium hydroxide, i.e., $Zr(OH)_4$, and hydrated zirconia. The expression, hydrated zirconia, is intended to connote materials comprising zirconium atoms covalently linked to other zirconium atoms via bridging oxygen atoms, i.e., Zr—O—Zr, further comprising available surface hydroxy groups. These available surface hydroxyl groups are believed to react with the source of an anion of a Group IVB metal, such as tungsten, to form the present acidic catalyst component. As suggested in the aforementioned article by K. Arata and M. Hino in *Proceedings 9th International Congress on Catalysis*, 4, 1727–1735 (1988), precalcination of $Zr(OH)_4$ at a temperature of from about 100° C. to about 400° C. results in a species which interacts more favorably with tungstate. This precalcination is believed to result in the condensation of ZrOH groups to form a polymeric zirconia species with surface hydroxyl groups. This polymeric species is referred to herein as a form of a hydrated zirconia.

Treatment of hydrated zirconia with an aqueous medium prior to contact with a source of tungstate may be preferable. More particularly, as demonstrated in co-pending U.S. Application Ser. No. 08/095,884, filed Jul. 22, 1993, refluxing hydrated zirconia in an aqueous medium having a pH of 7 or greater was beneficial. Without wishing to be bound by any theory, it is theorized that the hydrothermally-treated, hydrated zirconia is better because it has higher surface area. It is also theoretically possible that the hydrothermal treatment alters surface hydroxyl groups on the hydrated zirconia, possibly in a manner which promotes a more desirable interaction with the source of tungstate later used.

The hydrothermal conditions may include a temperature of at least 50° C., e.g., at least 80° C., e.g., at least 100° C. The hydrothermal treatment may take place in a sealed vessel at greater than atmospheric pressure. However, a preferred mode of treatment involves the use of an open vessel under reflux conditions. Agitation of hydrated Group IVB metal oxide in the liquid medium, e.g., by the action of refluxing liquid and/or stirring, promotes the effective interaction of the hydrated oxide with the liquid medium. The duration of the contact of the hydrated oxide with the liquid medium may be at least 1 hour, e.g., at least 8 hours. The liquid medium for this treatment may have a pH of 7 or greater, e.g., 9 or greater. Suitable liquid mediums include water, hydroxide solutions (including hydroxides of $NH_4^+$, $Na^+$, $Mg^{2+}$, and $Ca^{2+}$), carbonate and bicarbonate solutions (including carbonates and bicarbonates of $NH_4^+$, $Na^+$, $Mg^{2+}$, and $Ca^{2+}$), pyridine and its derivatives, and alkyl/hydroxyl amines.

Suitable sources for the oxyanion of the Group VIB metal, preferably molybdenum or tungsten, include, but are not limited to, ammonium metatungstate or metamolybdate, tungsten or molybdenum chloride, tungsten or molybdenum carbonyl, tungstic or molybdic acid and sodium tungstate or molybdate. The oxyanion of the Group VIB metal may optionally be replaced, at least in part, with sulfate.

The hydrogenation component of the present catalyst may be derived from Group VIII metals, such as platinum, iridium, osmium, palladium, rhodium, ruthenium, nickel, cobalt, iron and mixtures of two or more thereof. These components may optionally be mixed with components derived from Group IVA metals, preferably Sn, and/or components derived from Group VIIB metals, preferably rhenium and manganese. These components may be added to the catalyst by methods known in the art, such as ion exchange, impregnation or physical admixture. For example, salt solutions of these metals may be contacted with the remaining catalyst components under conditions sufficient to combine the respective components. The metal containing salt is preferably water soluble. Examples of such salts include chloroplatinic acid, tetraammineplatinum complexes, platinum chloride, tin sulfate and tin chloride.

The present catalyst may be prepared, for example, by impregnating the hydroxide or oxide, particularly the hydrated oxide, of the Group IVB metal with an aqueous solution containing an anion of the Group VIB metal, preferably tungstate or molybdate, followed by drying. Calcination of the resulting material may be carried out, preferably in an oxidizing atmosphere, at temperatures from about 500° C. to about 900° C., preferably from about 700° C. to about 850° C., and more preferably from about 750° C. to about 825° C. The calcination time may be up to 48 hours, preferably for about 0.5–24 hours, and more preferably for about 1.0–10 hours. In a most preferred embodiment, calcination is carried out at about 800° C. for about 1 to about 3 hours. The hydrogenation component of the catalyst (e.g., Group VIII metal, Group VIIB metal, etc.) may be added after or before the calcination step by techniques known in the art, such as impregnation, coimpregnation, coprecipitation, physical admixture, etc. The hydrogenation component may also be combined with the remaining catalyst components before or after these remaining components are combined with a binder or matrix material as described hereinafter.

When a source of the hydroxide or hydrated oxide of zirconium is used, calcination, e.g., at temperatures greater than 500° C., of the combination of this material with a source of an oxyanion of tungsten may be needed to induce the theorized chemical reaction which imparts the desired degree of acidity to the overall material. However, when more reactive sources of zirconia are used, it is possible that such high calcination temperatures may not be needed.

In the present catalyst, of the Group IVB oxides, zirconium oxide is preferred; of the Group VIB anions, tungstate is preferred; and of the hydrogenation components, platinum and/or platinum-tin are preferred.

Qualitatively speaking, elemental analysis of the present catalyst may reveal the presence of Group IVB metal, Group VIB metal and oxygen. The amount of oxygen measured in such an analysis will depend on a number of factors, such as the valence state of the Group IVB and Group VIB metals, the form of the hydrogenation component, moisture content, etc. Accordingly, in characterizing the composition of the present catalyst, it is best not to be restricted by any particular quantities of oxygen. In functional terms, the amount of Group VIB oxyanion in the present catalyst may be expressed as that amount which increases the acidity of the Group IVB oxide. This amount is referred to herein as an acidity increasing amount. Elemental analysis of the present catalyst may be used to determine the relative amounts of Group IVB metal and Group VIB metal in the catalyst. From these amounts, mole ratios in the form of $XO_2/YO_3$ may be calculated, where X is said Group IVB metal, assumed to be in the form $XO_2$, and Y is said Group VIB metal, assumed to be in the form of $YO_3$. It will be appreciated, however, that these forms of oxides, i.e., $XO_2$ and $YO_3$, may not actually exist, and are referred to herein simply for the purposes of calculating relative quantities of X and Y in the present catalyst. The present catalysts may have calculated mole ratios, expressed in the form of $XO_2/YO_3$, where X is at least one Group IVB metal (i.e., Ti, Zr, and Hf) and Y is at least one Group VIB metal (i.e., Cr, Mo, or W), of up to 1000, e.g., up to 300, e.g., from 2 to 100, e.g., from 4 to 30.

The amount of hydrogenation component may be that amount which imparts or increases the catalytic ability of the overall material to catalytically hydrogenate benzene. This amount is referred to herein as a catalytic amount. Quantitatively speaking, the present catalyst may comprise, for example, from about 0.001 to about 5 wt %, e.g., from about 0.1 to about 2 wt %, of the hydrogenation component, especially when this component is a noble metal.

The present process may be carried out by contacting the hydrocarbon feed in either liquid or gas phase with the solid catalyst at temperatures less than 300° C., e.g., from about 30° C. to about 200° C., e.g., from about 100° C. to about 130° C., and at pressure in the range from about 50 psig to about 1500 psig. The process is carried out in the presence of hydrogen. The mole ratio of hydrogen to benzene may be in the range of about 0.5:10, e.g., about 1:3. The weight hourly space velocity (WHSV) may be from about 1 to about 30, e.g., from about 3 to about 15, based on the weight of the benzene feed and the total weight of the catalyst. The reaction conditions may be sufficient to convert at least 80% of the benzene in the feed to a product comprising at least 80 wt. % of tercyclohexane.

It may be desirable to incorporate the present catalyst with another material to improve its properties. Such materials include active and inactive materials and synthetic or naturally occurring zeolites as well as inorganic materials such as clays, silica, and/or metal oxides. The latter may be either naturally occurring or in the form of gelatinous precipitates, sols, or gels including mixtures of silica and metal oxides.

It is noted that the present catalyst need not contain any sulfate ion (U.S. Pat. No. 4,918,041), and therefore, when free of sulfate ion, is expected to be more stable and also to be much easier to regenerate than sulfated catalysts, such as the superacid sulfated catalysts referred to in the aforementioned article by K. Arata and M. Hino in *Proceedings 9th International Congress on Catalysis*, 4, 1727–1735 (1988).

A noble metal, when used in the present catalyst, provides a hydrogenation component to the catalyst. Metals having a strong hydrogenation function are preferred, especially platinum and the other noble metals such as palladium, rhodium, iridium, rhenium, although other metals capable of acting as a hydrogenation component may also be used, for example, nickel, tungsten or other metals of Group VIIIA of the Periodic Table (IUPAC Table), either singly, in mixtures or in combination with other metals. The amount of the noble metal component may be in the range 0.001 to 5 wt. % of the total catalyst, e.g., from 0.1 to 2 wt. %. Base metal hydrogenation components may be added in somewhat greater amounts. The hydrogenation component can be exchanged onto the support material, impregnated into it or physically admixed with it. If the metal is to be impregnated into or exchanged onto the support, it may be done, for example, by treating the support with a platinum metal-containing ion. Suitable platinum compounds include chloroplatinic acid, platinous chloride and various compounds containing the platinum ammine complex. The metal compounds may be either compounds in which the metal is present in the cation or anion of the compound; both types of compounds can be used. Platinum compounds in which the metal is in the form of a cation of cationic complex, e.g., $Pt(NH_3)_4Cl_2$ are particularly useful, as are anionic complexes such as the vanadate and metatungstate ions. Cationic forms of other metals are also useful since they may be exchanged onto the support or impregnated into it.

The catalyst may be subjected to a final calcination under conventional conditions in order to dehydrate the catalyst and to confer the required mechanical strength on the catalyst.

When a source of hydrogenation metal, such as $H_2PtCl_6$, is used as a source of a hydrogenation component in the present catalyst, it may be desirable to subject the present catalyst to extended reducing conditions, e.g., lasting more than 4 hours. Benefits of such extended reducing conditions are demonstrated in co-pending U.S. application Ser. No. 08/143,716, filed Nov. 1, 1993.

The present catalyst can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the catalyst can be extruded before drying or partially dried and then extruded. The present catalyst may be composited with a matrix material to form the finished form of the catalyst and for this purpose conventional matrix materials such as alumina, silica-alumina and silica are suitable with preference given to silica as a non-acidic binder. Other binder materials may be used, for example, titania, zirconia and other metal oxides or clays. The active catalyst may be composited with the matrix in amounts from 80:20 to 20:80 by weight, e.g., from 80:20 to 50:50 active catalyst:matrix. Compositing may be done by conventional means including mulling the materials together followed by extrusion or pelletizing into the desired finished catalyst particles.

The catalyst may be treated by conventional pre-sulfiding treatments, e.g., by heating in the presence of hydrogen sulfide, to convert oxide forms of the metal components to their corresponding sulfides.

Example

This Example describes the preparation and use of a platinum-containing, tungstate-modified zirconia ($Pt/WO_x/ZrO_2$) catalyst.

Ammonium metatungstate (17.5 wt. % W target loading) was impregnated on hydrous zirconia. The hydrous zirconia was prepared by dissolving $ZrOCl_2$ in water, precipitating out with $NH_4OH$, and subsequently refluxing the precipitate in water adjusted to pH ~9 with base. After W impregnation, the catalyst was calcined at 825° C. in air for 3 hours. Pt was then impregnated onto the catalyst with $H_2PtCl_6$ solution (target Pt loading was 0.5 wt. %) and the final catalyst calcined at 300° C. in air for 3 hours.

In the catalytic tests, benzene was processed over the $Pt/WO_x/ZrO_2$ material at conditions of 150 psig, 3–15 WHSV, 1–3 mol/mol $H_2$/benzene, and 100°–130° C. The results are given in Table 1. The data clearly indicate $Pt/WO_x/ZrO_2$ to be a highly active (>90% conversion) and selective (85–98% selectivity) catalyst for conversion of benzene to tercyclohexanes.

TABLE 1

| Conditions | | | | | | | | | | | |
|---|---|---|---|---|---|---|---|---|---|---|---|
| Temp, °C. | | 60 | 60 | 60 | 90 | 100 | 100 | 130 | 130 | 130 | 130 |
| Psg | | 150 | 150 | 150 | 150 | 150 | 150 | 150 | 150 | 150 | 150 |
| WHSV | | 15 | 10 | 10 | 6 | 6 | 15 | 3 | 6 | 3 | 15 |
| H Benzene | | 1 | 1 | 3 | 3 | 3 | 1 | 3 | 3 | 1 | 1 |
| Product | Feed | | | | | | | | | | |
| $C_6$— Gas | | 0.00 | 0.00 | 0.00 | 0.07 | 0.20 | 0.01 | 0.13 | 0.12 | 0.05 | 0.05 |
| Cyclohexane | | 5.81 | 8.24 | 8.07 | 25.91 | 3.25 | 1.11 | 2.76 | 2.75 | 2.15 | 1.72 |
| Benzene | 100.00 | 82.74 | 76.93 | 63.17 | 23.08 | 1.73 | 5.53 | 4.65 | 6.56 | 9.63 | 8.78 |
| Phenylcyclohexane | | 0.00 | 0.00 | 0.00 | 1.14 | 11.37 | 0.80 | 1.92 | 4.30 | 0.60 | 1.43 |
| | | 0.00 | 0.00 | 0.00 | 0.87 | 0.00 | 0.00 | 0.00 | 0.00 | 0.00 | 0.00 |
| Benzene Trimer | | 11.45 | 14.83 | 28.76 | 48.93 | 83.46 | 92.55 | 90.54 | 86.26 | 87.56 | 88.03 |
| Total | 100.00 | 100.00 | 100.00 | 100.00 | 100.00 | 100.00 | 100.00 | 100.00 | 100.00 | 100.00 | 100.00 |
| % Benzene Conv. | | 17.26 | 23.07 | 36.83 | 76.92 | 98.27 | 94.47 | 95.35 | 93.44 | 90.37 | 91.22 |
| % Selectivity | | | | | | | | | | | |
| cyclo $C_6$ | | 33.64 | 35.70 | 21.91 | 33.68 | 3.31 | 1.18 | 2.89 | 2.95 | 2.38 | 1.88 |
| Dimer | | 0.00 | 0.00 | 0.00 | 1.48 | 11.56 | 0.85 | 2.02 | 4.60 | 0.66 | 1.56 |
| Trimer | | 66.35 | 64.29 | 78.08 | 63.61 | 84.93 | 97.97 | 94.95 | 92.31 | 96.89 | 96.50 |

What is claimed is:

1. A process for preparing tercyclohexane, said process comprising passing hydrogen and benzene under sufficient conversion conditions over a catalyst comprising an acidic solid and a hydrogenation component, wherein said acidic solid comprises a Group IVB metal oxide modified with an oxyanion of a Group VIB metal.

2. A process according to claim 1, wherein the molar ratio of $H_2$ to benzene in the feed is from about 0.5 to about 10.

3. A process according to claim 1, wherein the molar ratio of $H_2$ to benzene in the feed is from about 1 to about 3.

4. A process according to claim 1, wherein said conversion conditions include a temperature of from about 30° C. to about 200° C.

5. A process according to claim 1, wherein said conversion conditions include a temperature of from about 100° C. to about 130° C.

6. A process according to claim 1, wherein said conversion conditions include a pressure of from about 50 psig to about 300 psig.

7. A process according to claim 1, wherein said conversion conditions include a weight hourly space velocity of from about 1 to about 30, based on the weight of the benzene feed and the total weight of the catalyst.

8. A process according to claim 1, wherein said conversion conditions include a weight hourly space velocity of from about 3 to about 15, based on the weight of the benzene feed and the total weight of the catalyst.

9. A process according to claim 1, wherein said Group IVB metal is Zr and wherein said Group VIB metal is W.

10. A process according to claim 1, wherein said hydrogenation component comprises a noble metal.

11. A process according to claim 10, wherein said noble metal is Pt.

12. A process for preparing tercyclohexane, said process comprising the steps of:
(a) passing hydrogen and benzene under sufficient conversion conditions over a catalyst comprising an acidic solid and a noble metal, wherein said acidic solid comprises an oxide of zirconium modified with an oxyanion of tungsten; and
(b) recovering tercyclohexane.

* * * * *